(12) United States Patent
Nakamitsu

(10) Patent No.: US 10,786,384 B2
(45) Date of Patent: *Sep. 29, 2020

(54) SHOULDER BRACE FOR SIMPLE-PENDULUM MOTION

(71) Applicant: Shin-ichi Nakamitsu, Fukuoka (JP)

(72) Inventor: Shin-ichi Nakamitsu, Fukuoka (JP)

( * ) Notice: Subject to any disclaimer, the term of this patent is extended or adjusted under 35 U.S.C. 154(b) by 467 days.

This patent is subject to a terminal disclaimer.

(21) Appl. No.: 15/518,903

(22) PCT Filed: Jul. 29, 2015

(86) PCT No.: PCT/JP2015/071537
§ 371 (c)(1),
(2) Date: Oct. 9, 2017

(87) PCT Pub. No.: WO2017/017815
PCT Pub. Date: Feb. 2, 2017

(65) Prior Publication Data
US 2018/0133047 A1 May 17, 2018

(51) Int. Cl.
*A61F 5/40* (2006.01)
*A61F 5/37* (2006.01)
(Continued)

(52) U.S. Cl.
CPC ............ *A61F 5/3753* (2013.01); *A61F 5/373* (2013.01); *A61F 5/3738* (2013.01); *A61F 5/40* (2013.01);
(Continued)

(58) Field of Classification Search
CPC ...... A61F 5/373; A61F 5/3723; A61F 5/3738; A61F 5/3753; A61F 5/40; A61F 5/37;
(Continued)

(56) References Cited

U.S. PATENT DOCUMENTS 3,841,542 A * 10/1974 Hogensen, Jr. ............ A45F 5/00
224/586
5,651,143 A * 7/1997 Zehrung ............ A47D 13/025
2/16
(Continued)

FOREIGN PATENT DOCUMENTS

DE 43 14 785 C1 * 6/1993
JP 2003-10219 A 1/2003
(Continued)

OTHER PUBLICATIONS

Sep. 1, 2015, International Search Report of the International Searching Authority from Japan Patent Office in PCT/JP2015/071537, which is the international application to which this U.S. application claims the benefit of priority.
Sep. 1, 2015, Written Opinion of the International Searching Authority from Japan Patent Office in PCT/JP2015/071537, which is the international application to which this U.S. application claims the benefit of priority.

*Primary Examiner* — Rachael E Bredefeld
*Assistant Examiner* — Camtu T Nguyen
(74) *Attorney, Agent, or Firm* — Kolitch Romano LLP

(57) ABSTRACT

A shoulder brace can be fitted to a patient having an externally injured shoulder in the initial stage of treatment and which enables the patient to make motions in directions suitable for early rehabilitation exercises for the injured shoulder. The shoulder brace is fitted to the patient having the externally injured shoulder in a physiological reference position where the elbow joint of the patient is flexed by an angle of 90° in the frontward direction and the shoulder is internally rotated by an angle of 30°.

6 Claims, 8 Drawing Sheets

(51) Int. Cl.
*A61H 1/02* (2006.01)
*A61F 5/01* (2006.01)
(52) U.S. Cl.
CPC ......... *A61H 1/0277* (2013.01); *A61H 1/0281* (2013.01); *A61F 5/013* (2013.01); *A61H 2201/1269* (2013.01); *A61H 2201/165* (2013.01); *A61H 2201/1614* (2013.01); *A61H 2201/1635* (2013.01)
(58) Field of Classification Search
CPC ................ A61H 1/0277; A61H 1/0281; A61H 2201/1269; A61H 2201/1614; A61H 2201/1635; A61H 2201/165
See application file for complete search history.

(56) References Cited

U.S. PATENT DOCUMENTS

2003/0135141 A1    7/2003   Berhorst
2015/0190270 A1*   7/2015   Boone ................... A61F 5/3738
                                                                         602/4

FOREIGN PATENT DOCUMENTS

JP       2004-261531 A    9/2004
JP       2009-504295 A    2/2009

* cited by examiner

Fig. 1
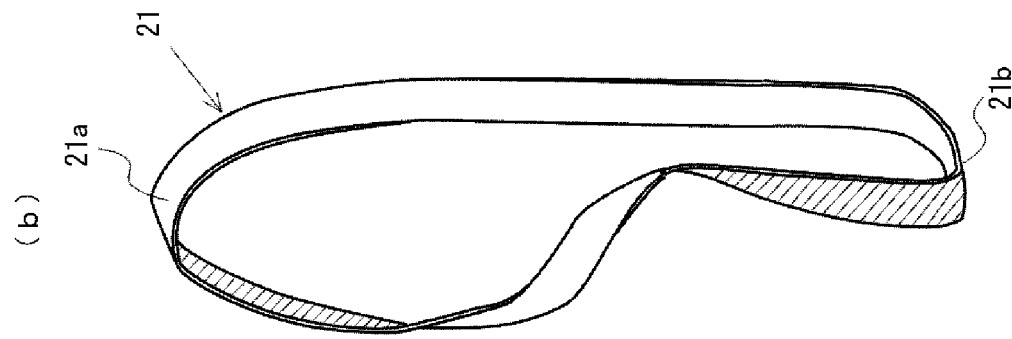
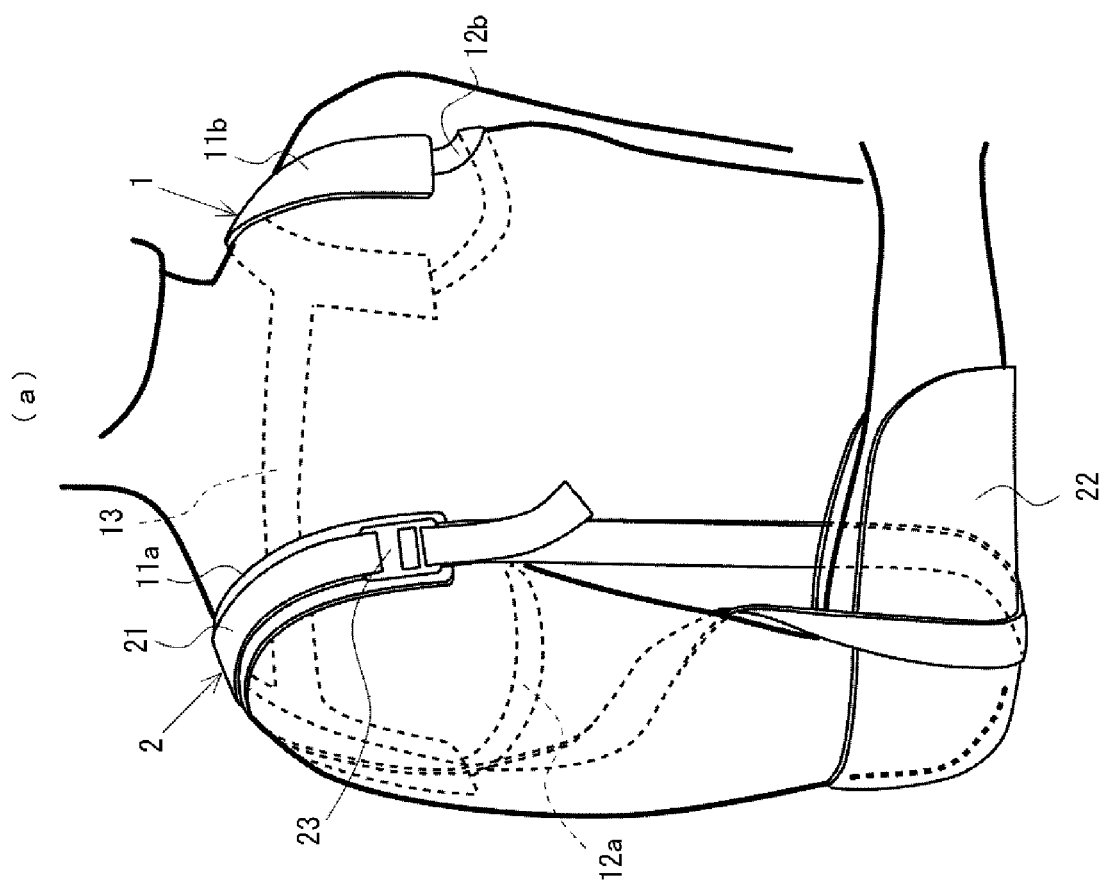

Fig. 2
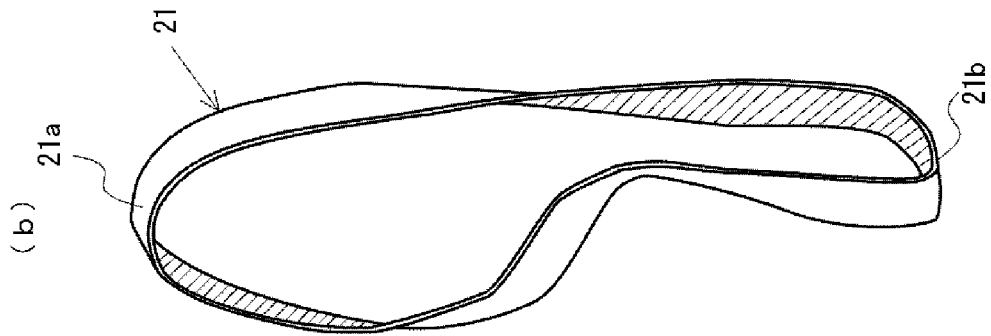
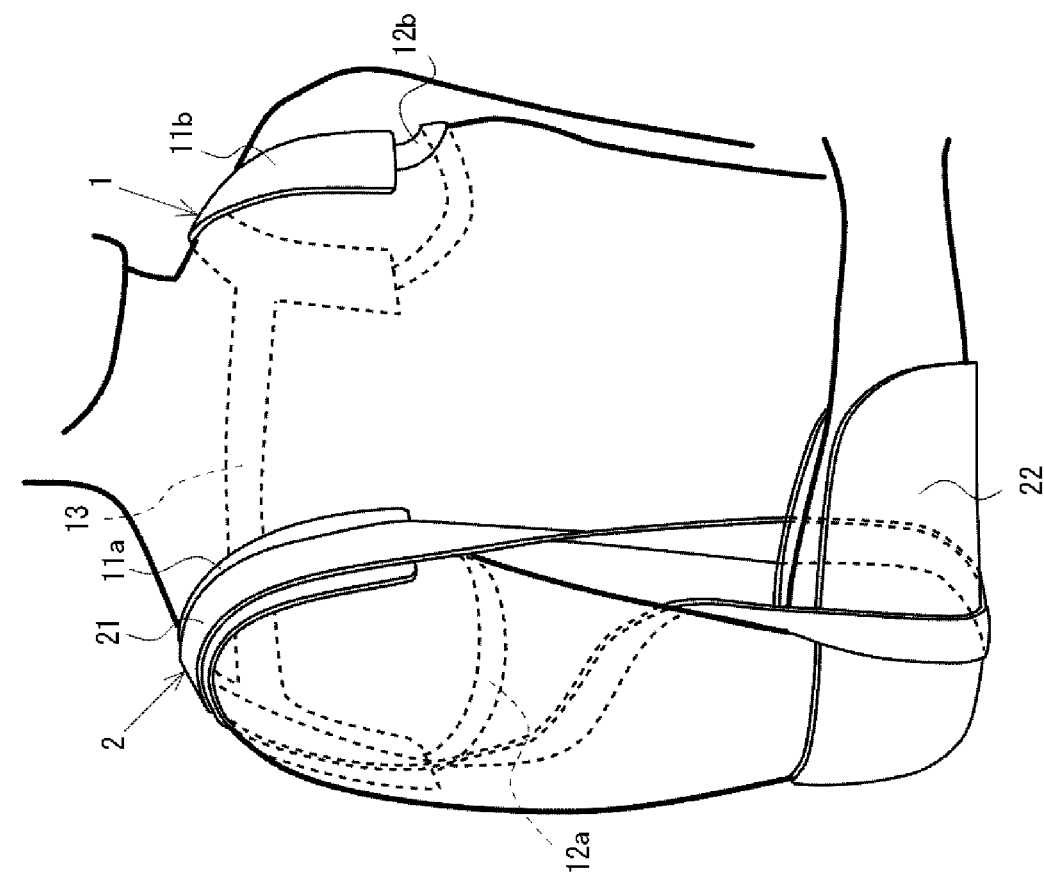

Fig. 5
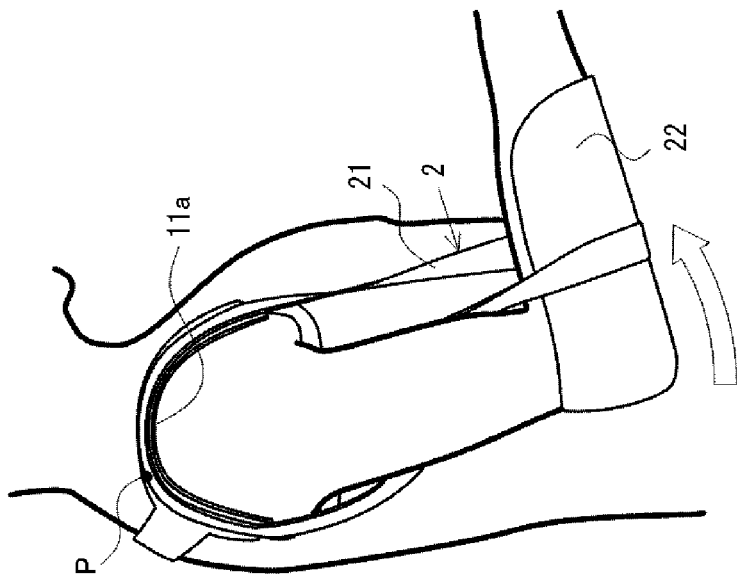
(c)
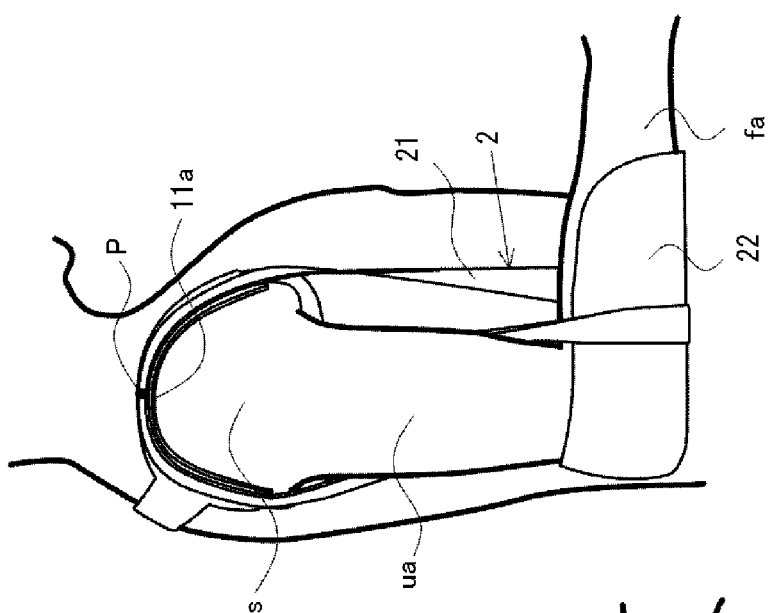
(a)
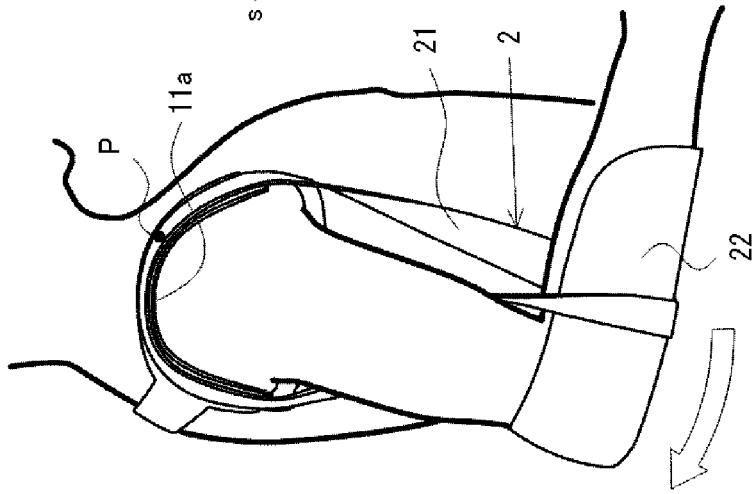
(b)

Fig. 8
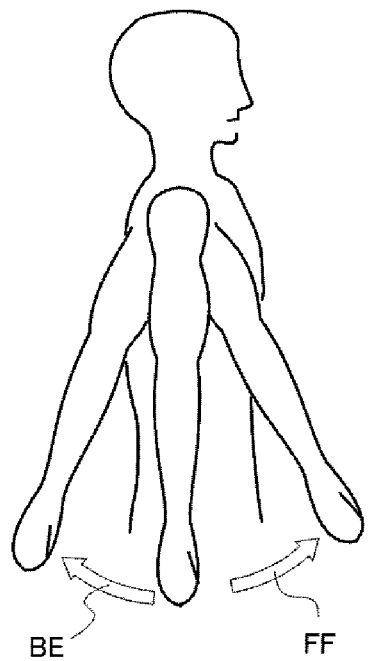
(a)
BE    FF
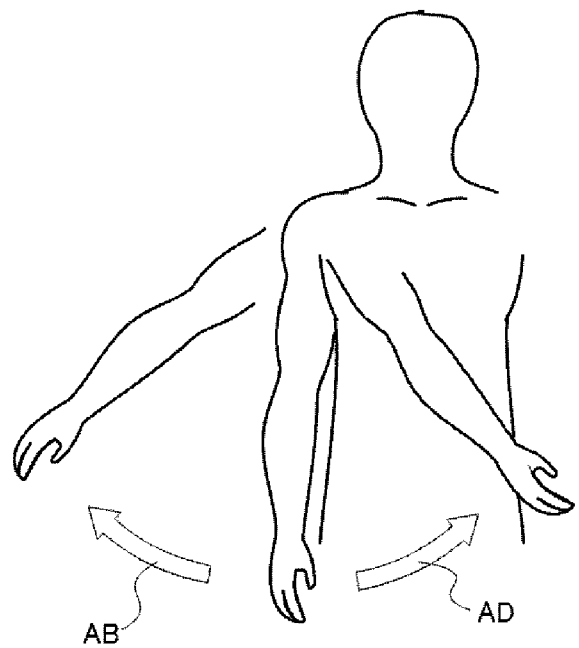
(b)
AB    AD
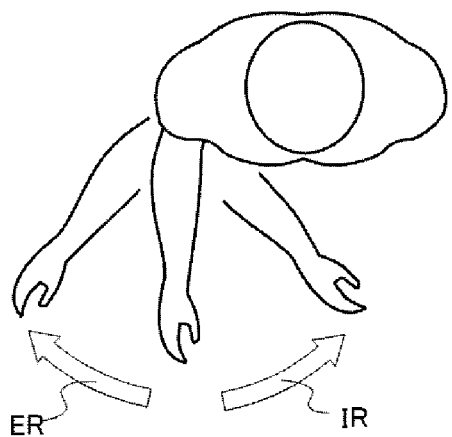
(c)
ER    IR

SHOULDER BRACE FOR SIMPLE-PENDULUM MOTION

CROSS-REFERENCE TO RELATED APPLICATION

This application is a national phase application of PCT/JP2015/071537, filed Jul. 29, 2015, which is hereby incorporated by reference.

FIELD

The present invention relates to a shoulder brace which is fitted to a patient having an externally injured shoulder, for example, a patient suffering proximal humerus fracture or the like. Particularly, it relates to a shoulder brace which has both the function of immobilizing an injured shoulder immediately after the patient has injured the shoulder or undergone an operation on the shoulder and the function of enabling the patient to take early rehabilitation exercises for the shoulder.

BACKGROUND

The shoulder is a part formed by the proximal humerus end, the scapula and the distal clavicle end. The scapulohumeral joint includes, as the intrinsic muscles, the rotator cuff, the joint capsule and the coracohumeral ligament. As the extrinsic muscles around it, there are many kinds of muscles such as the deltoid muscle, the biceps brachii, the triceps brachii, the pectoralis major and the trapezius. The above muscles act on the glenohumeral joint, the acromioclavicular joint and the scapulothoracic joint, and thereby, affect the movements of the shoulder and the upper arm. The present invention offers a brace for immobilizing an externally injured shoulder after the external injury such as proximal humerus fracture, rotator-cuff injury, acromioclavicular joint dislocation, shoulder joint dislocation and distal clavicle fracture. The shoulder brace is also employed for giving aftertreatment for the externally injured shoulder.

The shoulder joint is a multiaxial joint called a ball-and-socket joint and has a wide range of motion. Besides, to the periphery thereof, many kinds of muscles are attached, thereby easily causing the shoulder joint to make various motions. In consideration of the above, in the initial stage of treatment immediately after an injury or an operation, it is conventionally necessary to immobilize not only the shoulder but also the elbow, the forearm and the wrist over the wide range. Hence, braces are in general use which include a strap linking those parts to the neck or the shoulder on the unaffected-part side.

For example, U.S. Patent Application Publication No. 2003-0135141, Japanese Patent Laid-Open Publication No. 2003-10219, and Japanese Patent Laid-Open Publication No. 2004-261531 offer braces for immobilizing the affected part in the above method. U.S. Patent Application Publication No. 2003-0135141 discloses a brace which includes two straps linking a shoulder pad and a forearm holder. Japanese Patent Laid-Open Publication No. 2003-10219 discloses a brace which includes a strap set over the shoulder and a supporting portion arranged at both ends of the strap, the supporting portion supporting the wrist and the forearm. Japanese Patent Laid-Open Publication No. 2004-261531 discloses a brace for immobilizing the shoulder and the forearm to the trunk with the elbow joint flexed at an angle of 90°. In general, as given by U.S. Patent Application Publication No. 2003-0135141 and Japanese Patent Laid-Open Publication No. 2003-10219, almost all braces are designed so that the forearm can be flexed on the elbow joint and be located in the right-and-left directions in front of the trunk.

In the shoulder including numerous bones and muscles, contracture may be caused when the shoulder is kept immobilized. Therefore, it would be important to begin rehabilitation early while securely stabilizing the affected part. A patient usually takes rehabilitation exercises after removing a brace for immobilizing the shoulder, and takes a passive exercise, an active assistant exercise, an active exercise and a resistance exercise step-by-step in this order. As the apparatus for rehabilitation, a CPM (continuous passive motion) apparatus including a driving mechanism is well known. The CPM apparatus is not designed such that a patient fits it constantly, and the CPM apparatus is used only when the patient takes a rehabilitation exercise.

FIG. 7 shows the Codman's pendular motion supposed to be made as an early rehabilitation exercise in the initial stage of treatment. In order to avoid a pain, a fracture and an invasion of a soft tissue and consider the safety of an affected part, this exercise is usually taken after the affected part is healed to a minimum level. The patient bends the trunk, puts the hand on the unaffected-part side onto a desk or the like so that the arm can support the body and freely hangs down the upper extremity on the affected-part side. Then, the patient moves the trunk to let the hanging upper extremity swing like a pendulum and continues doing the passive exercise. In this case, the pendular motion is composed of multiple pendular motions in the directions indicated by the arrows of the figure such as the front-and-back, right-and-left and rotational directions.

FIGS. 8(a) to 8(c) show a notation for movements of the shoulder joint in a three-dimensional space, which is defined by the Japanese Orthopaedic Association and the Japanese Association of Rehabilitation Medicine. The present invention refers to some terms written in the notation, and hence, all of those terms will be below described.

FIG. 8(a) shows a rotational motion on a plane parallel to the sagittal plane, and the front elevation denoted by reference character FF is called "forward flexion" while the back elevation denoted by reference character BE is called "backward extension". FIG. 8(b) shows a rotational motion on a plane parallel to the frontal plane, and the rotation in the direction away from the trunk which is denoted by reference character AB is called "abduction", while the rotation in the opposite direction denoted by reference character AD is called "adduction". FIG. 8(c) shows a rotational motion on the horizontal plane when the elbow joint is flexed frontward at an angle of 90°, and the rotation toward the outside denoted by reference character ER is called "external rotation" while the rotation in the opposite direction denoted by reference character IR is called "internal rotation".

If the upper extremity is set to a forward-flexion angle of 0°, an abduction angle of 0° and an internal-rotation angle of 0°, then the upper extremity is in the classical reference position of the shoulder. On the other hand, the physiological reference position of the shoulder corresponds to the position of a forward-flexion angle of 0°, an abduction angle of 0° and an internal-rotation angle of 30°. In the physiological reference position, the upper extremity (upper arm) is hanging down along the trunk with letting the tension out of it. This is because the scapular plane of a person is not parallel to the frontal plane and is inclined at an angle of 30° (i.e., the outside of the scapula is located forwarder than the inside thereof). The inclination angle of 30° varies slightly with the movement of the scapulae of a person when the person throws out the chest or hunches the back to the scapulae.

SUMMARY

The above conventional shoulder braces have the following problems that the shoulder braces:

are exclusively used for immobilizing an affected part and not originally applied to early rehabilitation exercises in which a patient fitted therewith moves the upper extremity or the upper arm;

may cause contracture, myotrophy and functional disorder in an affected part after a patient is fitted therewith over a long period of time;

make it difficult for a patient to move the upper extremity in the front-and-back directions when the forearm is located in the right-and-left directions in contact with the front of the trunk, even though it is easy to move the upper extremity in the right-and-left directions; and include a sling set on the forearm and the shoulder of a patient, the sling slipping or falling easily from the shoulder when the patient fitted with the sling takes exercise, and include a sling set on the neck of a patient, the sling easily causing a pain in the neck.

The Codman's pendular motion made by a patient after removing a shoulder brace in the initial stage of treatment has the following problems that the Codman's pendular motion:

may cause displacement of a fractured part in the shoulder of a patient because the upper extremity hangs down without support and thereby the force of gravity pulls the fractured part apart;

may cause inflammation of various muscles in the shoulder of a patient subjected to an invasion in an operation, or cause a pain in the muscles, because the patient makes pendular motions in all directions while keeping the upper extremity hanging down;

may cause displacement of a fractured part in the shoulder of a patient by an upward tensile force produced when the patient swings the upper extremity in directions where various muscles in the shoulder are tensed while making pendular motions in all directions;

should not be made immediately after a patient is injured or undergoes an operation, in other words, it should be made after the affected part is healed to a minimum level in the initial stage of treatment;

cannot be made by some patients who are unable to bend forward because of their ages or physical conditions; and is supposed to be made by a patient after removing the brace fitted to the patient.

In view of the present situation described above, it is an object of the present invention to provide a shoulder brace which is fitted to a patient having an externally injured shoulder in the initial stage of treatment and which enables the patient, without removing the shoulder brace, to make motions in directions suitable for early rehabilitation exercises for the injured shoulder.

In order to solve the problems, the present invention provides the following configurations. The reference numerals and characters in parentheses correspond to those in the figures described later and is given for reference.

A shoulder brace for a simple-pendulum motion according to a first aspect of the present invention which is fitted to a patient having an externally injured shoulder in a physiological reference position where the elbow joint of the patient is flexed by an angle of 90° in the frontward direction and the shoulder is internally rotated by an angle of 30°, includes: a first layer (1) including at least: shoulder attachment portions (11a, 11b) attached to both shoulders respectively, the shoulder attachment portions (11a, 11b) each having a predetermined width and being arranged in the frontward and backward directions; and a back-side linking portion (13) extending in the rightward and leftward directions and linking back-end parts of the right and left shoulder attachment portions (11a, 11b); and a second layer (2) including at least a ringed sling (21) having a predetermined width, the sling (21): running below from the front end of a shoulder portion (21a) of the sling (21), the shoulder portion (21a) being placed on the shoulder attachment portion (11a) of the first layer (1) on the affected-part side, up to the ulnar side of the forearm adjacent to the elbow; running from the ulnar side of the forearm across the lower-surface side of the forearm up to the radial side of the forearm; running from the radial side of the forearm across the front of the upper arm; and running through the armpit up to the back end of the shoulder portion (21a), wherein the patient fitted with the shoulder brace is able to take a simple-pendulum exercise in the frontward and backward directions while retaining the forearm at the shoulder internal-rotation angle of the physiological reference position.

According to an embodiment of the above aspect, the second layer (2) is provided with a forearm trough (22) for supporting the forearm, and the sling (21) runs across the lower-surface side of the forearm trough (22).

According to an embodiment of the above aspect, the first layer (1) is provided with armpit band portions (12a, 12b) each linking, through the armpit, the front end and the back end of each of the right and left shoulder attachment portions (11a, 11b) respectively.

According to an embodiment of the above aspect, the first layer (1) is provided with: an armpit band portion (12b) linking, through the armpit, the front end and the back end of the shoulder attachment portion (11b) of the first layer (1) on the unaffected-part side alone; and a front-side linking portion (15) extending in the rightward and leftward directions and linking front-end parts of the right and left shoulder attachment portions (11a, 11b).

The shoulder brace for a simple-pendulum motion according to the present invention enables a patient fitted with the shoulder brace to take a simple-pendulum exercise in the frontward and backward directions, without removing the shoulder brace, in the initial stage of treatment. The simple-pendulum exercise in the frontward and backward directions is taken by making the motion of only the forward flexion and the backward extension while retaining the forearm at the shoulder internal-rotation angle of the physiological reference position. In the simple-pendulum exercise, the motions are made in the directions which are safe for the injured shoulder, thereby less frequently causing displacement of the fractured part. Therefore, a patient fitted with the shoulder brace according to the present invention can take the simple-pendulum exercise before the Codman's pendular motion is permitted, for example, even one or two days after the patient is injured or undergoes an operation. Hence, the shoulder brace according to the present invention is capable of shortening the period required for wholly retaining and immobilizing an injured shoulder of a patient extremely immediately after the patient is injured or undergoes an operation.

In addition, the shoulder brace according to the present invention enables a patient fitted therewith to take the above exercise in a standing position and a sitting position, thereby reducing the burden. Besides, the elbow joint of a patient is flexed by an angle of 90° to direct the forearm frontward, enabling the patient to use the hand and thereby lessening the hindrance to the activities of daily living.

Furthermore, the shoulder brace according to the present invention includes the second layer provided with the sling, and the sling has the function of retaining the upper extremity in the above physiological reference position and letting the patient take the simple-pendulum exercise. The sling runs through a predetermined route on the shoulder, the upper arm and the forearm, and hence, has a predetermined twist as a whole. The twisted sling applies force to the shoulder, the upper arm and the forearm, and thereby, restricts the movements thereof so that they can move only in specified directions. As a result, the sling suppresses movements of the muscles for making the adduction and abduction motions and making the internal-rotation and external-rotation motions by wide angles, those motions tending to cause displacement of a fractured part. Particularly, the rotator cuff as the main intrinsic muscle used for the abduction is frequently damaged by an injury or an operation, and this is the reason why the rotator cuff should not be contracted. In summary, the sling of the second layer allows the muscles to move only in the directions safe for the muscles, in other words, it prevents the muscles from moving in the unsafe directions.

Moreover, the unaffected rotator cuff of a patient also has the function of retaining the humeral head in the afferent position. Instead of the rotator cuff subjected to suppression of the movement thereof, the sling of the second layer is capable of retaining the humeral head in the afferent position. This function enables the patient to take the exercise stably while retaining the humeral head in the afferent position.

In addition, the sling of the second layer supports the elbow of a patient to retain the upper extremity constantly, thereby keeping the upper extremity from hanging down. This prevents displacement of a fractured part in the shoulder which may be caused by the weight of the hanging upper extremity in the Codman's pendular motion.

Furthermore, the first layer functions as a base brace for stably maintaining the functional shape of the sling of the second layer. The first layer includes the shoulder attachment portion for setting a shoulder portion of the sling of the second layer, and the shoulder attachment portion is designed to prevent the sling of the second layer from slipping in the right-and-left directions and lead it to slide easily in the front-and-back directions on the shoulder of a patient. Besides, the shoulder attachment portion of the first layer is relatively wide and is individually provided on each shoulder of the patient. Therefore, the patient can take the simple-pendulum exercise without concentrating the burden on a specified part of the shoulder on the affected-part side, thereby reducing the pain in the shoulder.

BRIEF DESCRIPTION OF THE DRAWINGS

FIG. 1(a) is a perspective view of a shoulder brace fitted to a patient according to an embodiment of the present invention.

FIG. 1(b) is a perspective view of a sling in a specified shape which is included in a second layer of the shoulder brace.

FIG. 2(a) is a perspective view of the shoulder brace of FIG. 1(a) showing the sling of the second layer fitted to a patient in a shape different from FIG. 1(a).

FIG. 2(b) is a perspective view of the sling in the shape which is included in the second layer of the shoulder brace of FIG. 2(a).

FIGS. 5(a) to 5(c) are side views of the shoulder brace fitted to the patient shown in FIG. 2(a) for the purpose of explaining advantages of the present invention.

FIGS. 8(a) to 8(c) show a notation for movements of the shoulder joint of a person in a three-dimensional space.

MODE FOR CARRYING OUT THE INVENTION

A shoulder brace according to an embodiment of the present invention will be below described with reference to the figures. FIG. 1(a) is a perspective view of the shoulder brace fitted to a patient according to the embodiment of the present invention. FIG. 1(b) is a perspective view of a sling in a specified shape which is included in a second layer of the shoulder brace.

FIG. 2(a) is a perspective view of the shoulder brace of FIG. 1(a) showing the sling of the second layer fitted to a patient in a shape different from FIG. 1(a). FIG. 2(b) is a perspective view of the sling in the shape which is included in the second layer of the shoulder brace of FIG. 2(a).

Figure 3:
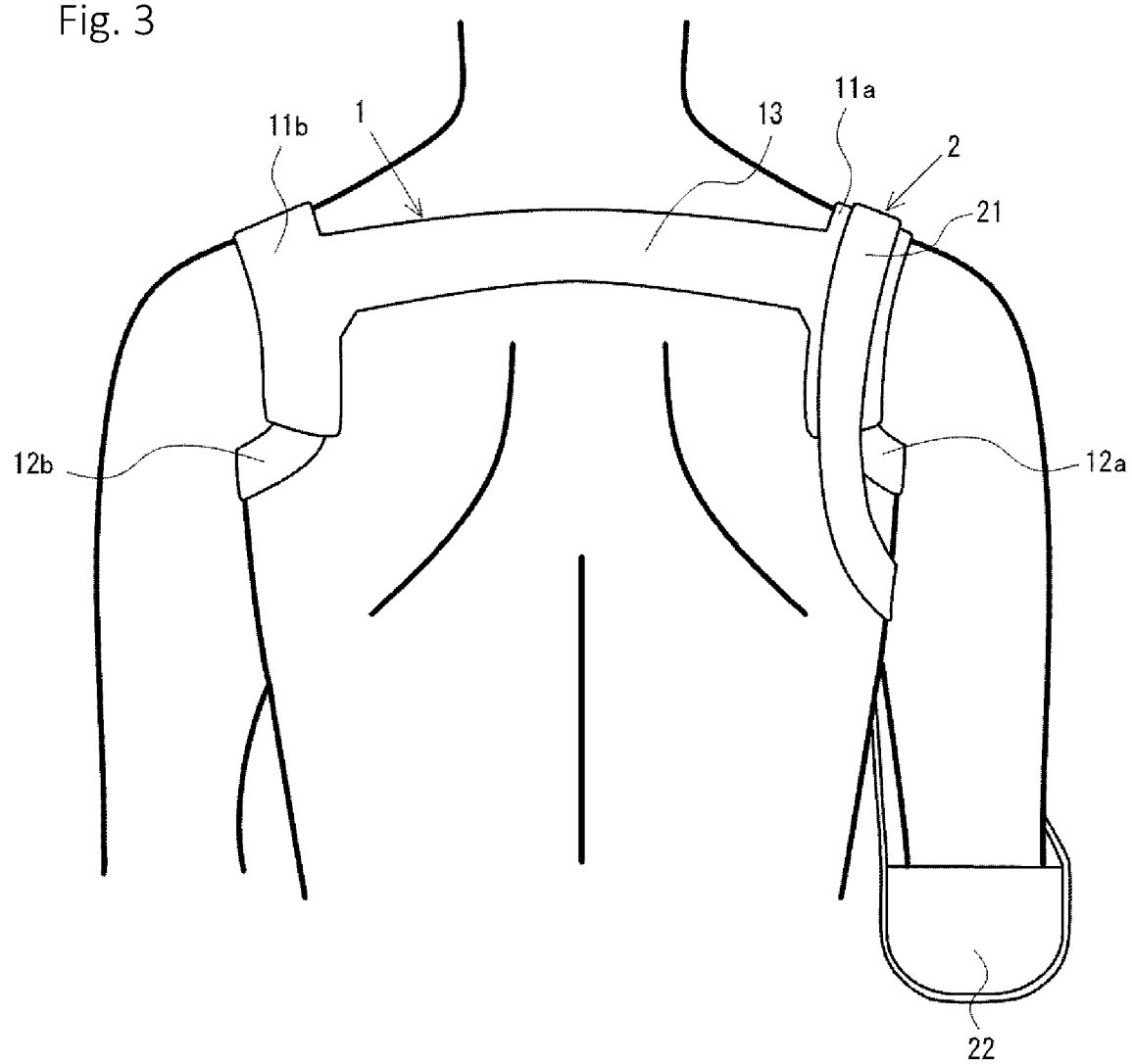
FIG. 3 is a back view of the shoulder brace fitted to the patient shown in FIG. 2(a).
Figure 4:
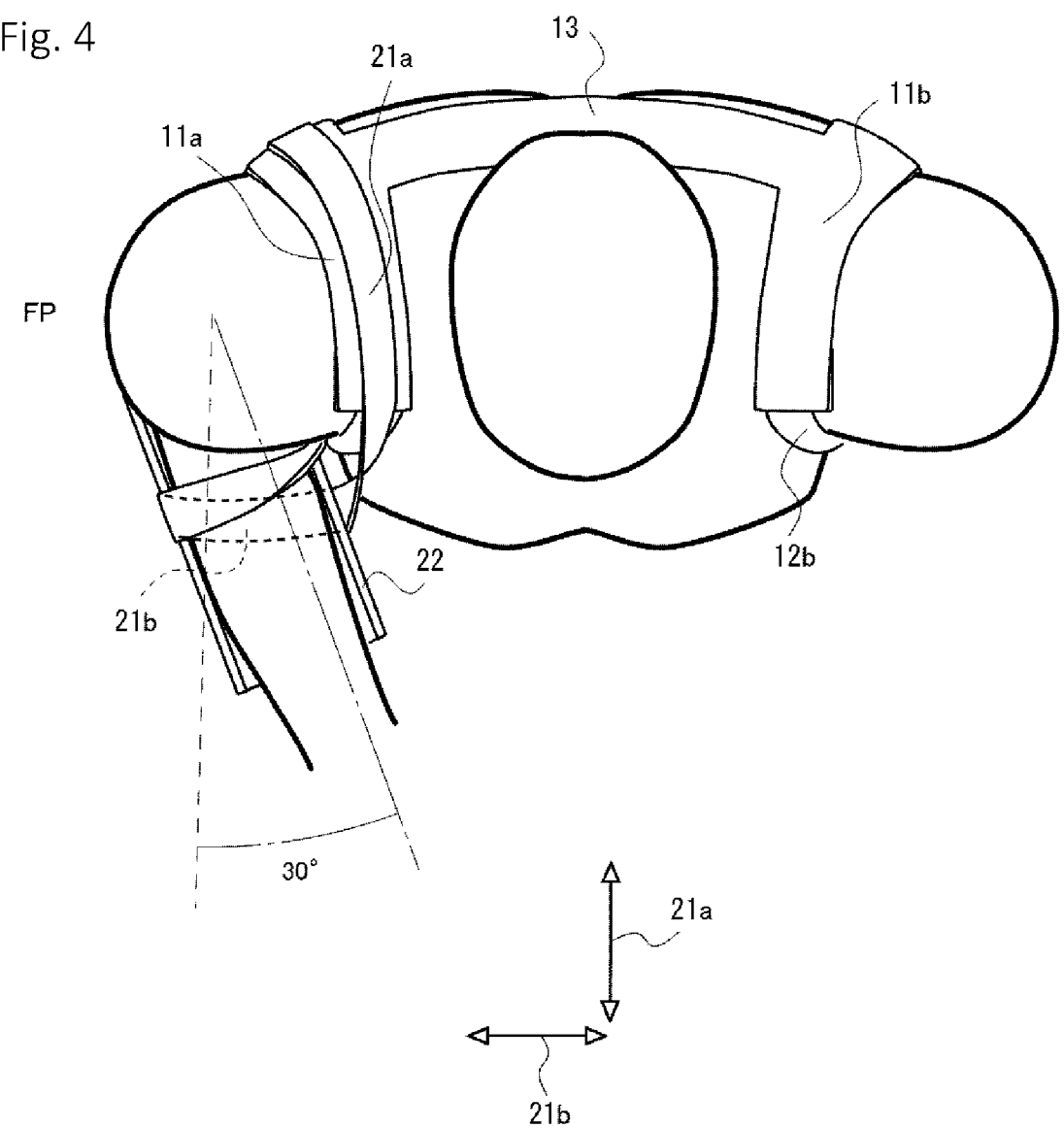
FIG. 4 is a top view of the shoulder brace fitted to the patient shown in FIG. 2(a).

FIG. 3 is a back view of the shoulder brace fitted to the patient shown in FIG. 2(a). FIG. 4 is a top view of the shoulder brace fitted to the patient shown in FIG. 2(a).

First, the configuration of the shoulder brace according to the embodiment of the present invention will be described with reference to FIGS. 1(a) and 1(b) to FIG. 4. The shoulder brace according to the embodiment of the present invention is formed by at least two component elements fitted to a patient with overlapping. The two component elements are not wholly arranged in layers with one being on top of the other and are named a first layer and a second layer in order from the lower layer. In FIGS. 1(a) and 1(b) to FIG. 4, reference numerals 1 and 2 denote the first layer and the second layer respectively which are the main component elements fitted to a patient for practical treatment.

In the figures, the right shoulder of the patient corresponds to the affected part (i.e., the right side corresponds to the affected-part side) and the left shoulder corresponds to the unaffected part (i.e., the left side corresponds to the unaffected-part side). Although only the shoulder on the one side corresponds to the affected part in the figures, the shoulder brace according to the present invention is also applicable to the case where both shoulders are affected. In that case, the right and left shoulders are each provided with the second layer.

The shoulder brace is fitted to a patient having an externally injured shoulder in a physiological reference position where the elbow joint of the patient is flexed by an angle of 90° in the frontward direction. The physiological reference position corresponds to the upper-extremity position of a forward-flexion angle of 0°, an abduction angle of 0° and an internal-rotation angle of 30°. The upper arm is hanging down naturally along the side of the trunk, and the forearm is internally rotated by an angle of 30° with respect to the direction perpendicular to a frontal plane FP (the internal-rotation direction is also called the "frontward direction" for the convenience of description). The above numerical values of the angles are not strict and have certain ranges (e.g., a range of plus or minus approximately 10 percent).

As shown in FIGS. 1(a) and 1(b) to FIG. 4, the first layer 1 includes at least: right and left shoulder attachment portions 11a and 11b attached to both shoulders respectively and arranged in the frontward and backward directions; and a back-side linking portion 13 extending in the rightward and leftward directions across the back of the patient and linking back-end parts of the right and left shoulder attachment portions 11a and 11b. The shoulder attachment portions 11a and 11b each have a predetermined width, and particularly, it is preferable that the shoulder attachment portion 11a on the affected-part side is wide enough to disperse the load.

At least the shoulder attachment portion 11b on the unaffected-part side is provided with an armpit band portion 12b which links, through the armpit, the front end and the back end thereof. On the other hand, the shoulder attachment portion 11a on the affected-part side is moderately fixed in a position thereof, because it is covered with a sling 21 of the second layer 2 and is linked via the back-side linking portion 13 to the shoulder attachment portion 11b. This dispenses with an armpit band portion 12a for the shoulder attachment portion 11a on the affected-part side. Consequently, as described later, the patient can take a simple-pendulum exercise advantageously without a hindrance which may be caused by the armpit band portion 12a. However, as shown in the figures, both of the right and left shoulder attachment portions 11a and 11b may be linked to the armpit band portions 12a and 12b respectively, thereby stably fitting the first layer 1 to the patient.

The second layer 2 includes at least a ringed sling 21 having a predetermined width, and the sling 21 is a closed ring having an untwisted-belt shape when the sling 21 is not fitted to the patient. On the affected-part side, the sling 21 is fitted, and the uppermost part (called a shoulder portion 21a of the sling 21) is placed in the front-and-back directions on the shoulder attachment portion 11a of the first layer 1. Preferably, the sling 21 may be narrower than the shoulder attachment portion 11a and be placed in a middle part in the width directions of the shoulder attachment portion 11a. If necessary, the sling 21 may be provided with an adjustment fitting 23 for adjusting the length of the sling 21.

As shown in FIGS. 1(a) and 1(b) to FIG. 4, especially in FIGS. 1(a) and 1(b) and FIGS. 2(a) and 2(b), the sling 21 is fitted to the patient in the following way. The sling 21: runs below substantially vertically from the front end of the shoulder portion 21a up to the ulnar side of the forearm adjacent to the elbow; runs from the ulnar side of the forearm across the lower-surface side of the forearm up to the radial side of the forearm (across the part of the reference numeral and character 21b of FIG. 4); runs from the radial side of the forearm across the front of the upper arm; and runs through the armpit up to the back end of the shoulder portion 21a.

As shown in FIGS. 1(b) and 2(b) which indicate only the sling 21, when the sling 21 is fitted to the patient, narrow parts are formed in middle parts of the ring, and the sling 21 is twisted as a whole at the narrow parts. The whole twists of the sling 21 can be seen in the top view of FIG. 4. The two blank arrows of FIG. 4 indicate, in plan view, the directions (substantially the front-and-back directions) in which the shoulder portion 21a of the sling 21 runs, and the directions (substantially the right-and-left directions) in which a portion 21b of the sling 21 across the lower-surface side of the forearm runs. The two arrows are substantially perpendicular to each other.

The sling 21 of the second layer 2 is fitted to the patient in this shape to apply force to the forearm and the upper arm on the affected-part side, thereby controlling the position of the forearm and the upper arm. As a result, the upper extremity on the affected-part side can be retained in the physiological reference position. Further, the sling 21 retains the elbow joint flexed by an angle of 90° in the frontward direction and the shoulder internally rotated by an angle of 30° in the physiological reference position. While retaining this position, the sling 21 allows the upper extremity to move only in the backward-extension and forward-flexion directions and prevents it from moving in the other directions.

In addition, the sling 21 runs below substantially vertically from the front end of the shoulder portion 21a and makes in contact with a part of the forearm adjacent to the elbow. The contact portion with the forearm is adjacent to the elbow, and hence, even if the flexion angle of the elbow joint varies around 90°, the variation will hardly affect the length of the sling 21. Accordingly, the sling 21 can be constantly kept tight.

In FIGS. 1(a) and 1(b), the shape of the sling 21 fitted to the patient differs from that of FIGS. 2(a) and 2(b), and the difference will be described with reference to FIGS. 1(b) and 2(b). In these figures, the reverse surface of the sling 21 is indicated by the oblique lines. In FIG. 1(b), the front surface of the sling 21 is exposed at the shoulder portion 21a, and the reverse surface thereof is exposed at the portion 21b on the lower-surface side of the forearm. In contrast, in FIG. 2(b), the front surface of the sling 21 is exposed at both the shoulder portion 21a and the portion 21b on the lower-surface side of the forearm. This difference is made by twisting the sling 21 at different local points thereof. The advantages of the present invention can be obtained regardless of the shapes of the sling 21 fitted to the patient.

FIGS. 5(a) to 5(c) are side views of the shoulder brace of FIG. 2(a) for the purpose of explaining the advantages of the present invention. FIG. 5(a) is a side view of the shoulder brace in the position of the patient shown in FIG. 2(a). The upper extremity is retained with the elbow joint flexed by an angle of 90° in the frontward direction and the shoulder internally rotated by an angle of 30°, in other words, it is retained in the physiological reference position. The patient in this position makes various motions of the trunk, thereby leading to a passive motion of the upper extremity in the front-and-back directions with the shoulder internally rotated by the above angle. The passive motion of the upper extremity in the front-and-back directions is a pendular motion which consist of the backward extension shown in FIG. 5(b) and the forward flexion shown in FIG. 5(c) and is supposed to be repeatedly made. This pendular motion is made only on the vertical plane including the vector of the shoulder internally rotated by an angle of 30°. In other words, the patient is prohibited from moving the upper extremity in any other direction, and hence, the pendular motion is a simple-pendulum motion.

In FIGS. 5(a) to 5(c), reference character P denotes a point in the shoulder portion of the sling 21 of the second layer 2. It can be seen that in the above simple-pendulum motion, the point P slides in the front-and-back directions on the shoulder attachment portion 11a of the first layer 1. In order to promote the simple-pendulum motion, it is preferable that the front surface of the shoulder attachment portion 11a of the first layer 1 facilitates a slide of the shoulder portion of the sling 21 in the front-and-back directions. On the other hand, in order to prevent the sling 21 from slipping down from the shoulder, it is preferable that the front surface of the shoulder attachment portion 11a hinders a slide of the shoulder portion in the right-and-left directions.

The simple-pendulum motion is made only in the directions which are safe for the injured shoulder, in other words, the simple-pendulum motion is not made in the prohibited directions where the motion may cause displacement of the fractured part or injury of the muscles. Therefore, the patient is fitted with the shoulder brace immediately after the patient is injured or undergoes an operation, so that the patient can take the simple-pendulum exercise from the point of time. This means that the patient can begin extremely early rehabilitation exercises. Further, the simple-pendulum motion is a passive motion which is naturally made when the patient moves the trunk variously, and thereby, the patient does not need to make the simple-pendulum motion intentionally. Still further, the simple-pendulum motion does not require that the patient should stay in a posture imposing a great burden thereon, so that the patient can take the simple-pendulum exercise even in either a standing position or a sitting position. Still further, since the patient is fitted with the shoulder brace according to the present invention immediately after the patient is injured or undergoes an operation, the period for wholly immobilizing the upper extremity of the patient is dispensable, thereby preventing contracture from developing in the shoulder.

Figure 6:
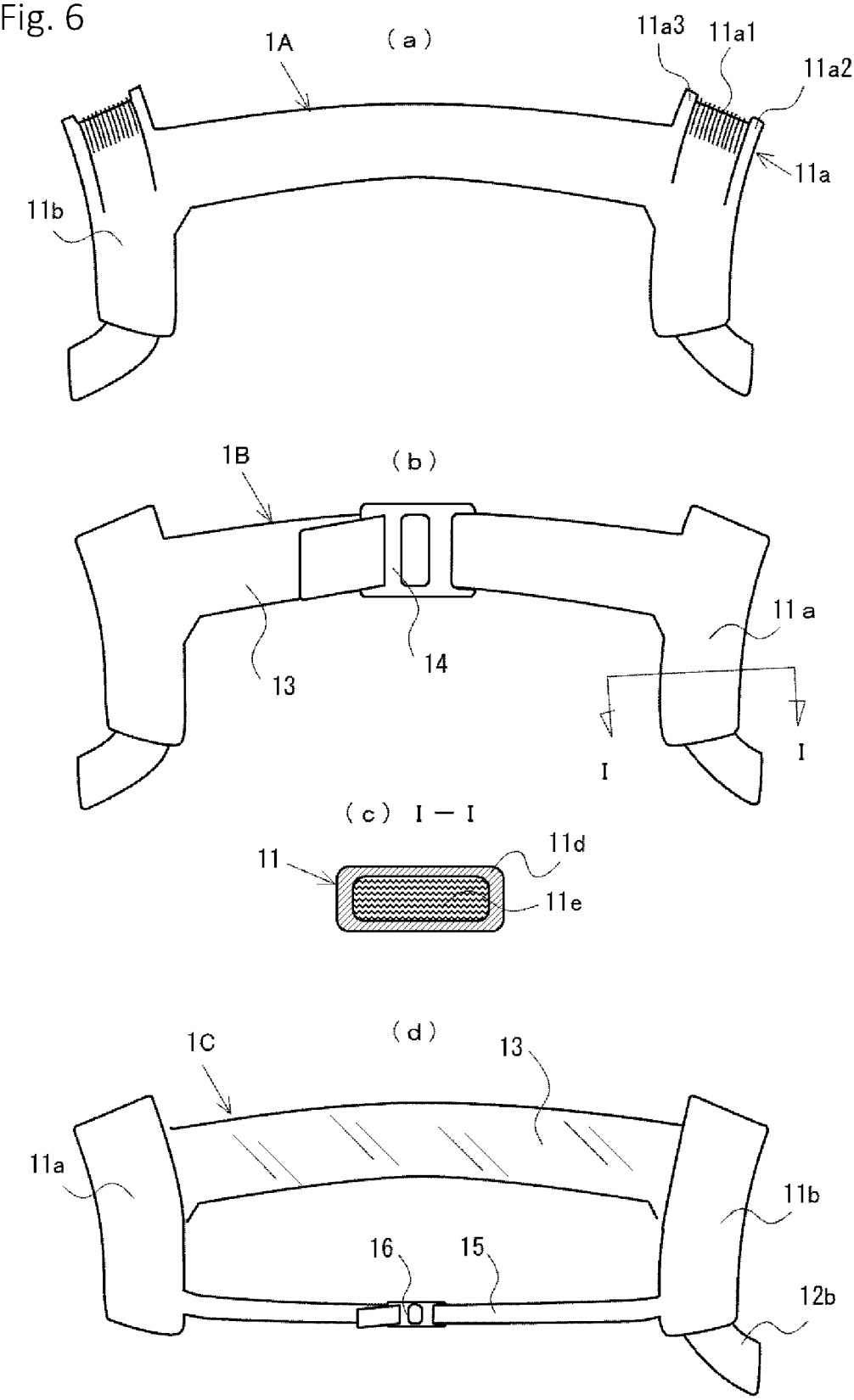
FIGS. 6(a) to 6(d) show variations of a first layer of the shoulder brace according to the present invention.
Figure 7:
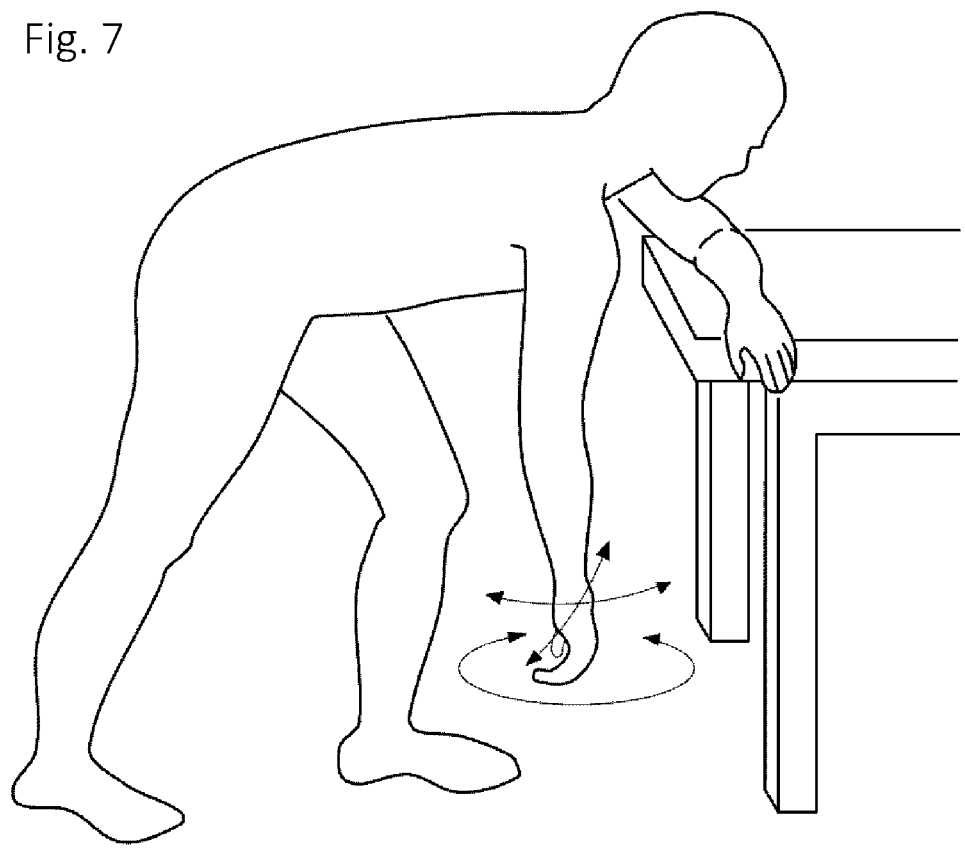
FIG. 7 is an illustration showing the Codman's pendular motion supposed to be made ahead of a passive exercise as an early physical therapy.

FIGS. 6(a) to 6(d) show variations of the first layer of the shoulder brace according to the present invention. FIG. 6(a) is a back view of a variation 1A of the first layer. In the variation 1A, the shoulder attachment portion 11a includes protrusive lines 11a2 and 11a3 formed along both edges in the width directions thereof respectively, and the protrusive lines 11a2 and 11a3 each protrude by a predetermined height. The protrusive lines 11a2 and 11a3 each have the function of a wall preventing the sling 21 from sliding in the right-and-left directions. Particularly, the protrusive line 11a2 on the outside is effective for preventing the sling 21 from slipping off the shoulder, and hence, only the protrusive line 11a2 on the outside may be formed in the shoulder attachment portion 11a. Besides, a front surface 11a1 of the shoulder attachment portion 11a is a surface coming in contact with the back surface of the sling 21, and in order to slide the sling 21 easily in the front-and-back directions, the front surface 11a1 may be formed with numerous narrow grooves extending in the front-and-back directions. In the figure, the shoulder attachment portion 11b on the unaffected-part side is also formed with such protrusive lines and grooves. The protrusive lines and grooves make it possible to employ the shoulder brace for both right and left shoulders. Basically, the protrusive lines and grooves are unnecessary on the unaffected-part side.

FIG. 6(b) is a back view of another variation 1B of the first layer. In the variation 1B, the back-side linking portion 13 is provided with an adjustment fitting 14 for adjusting the length thereof. FIG. 6(c) is a schematic sectional view along a line I-I in the variation 1B of FIG. 6(b), showing still another variation. The shoulder attachment portion 11a imposes a burden on the shoulder, and the burden needs to be reduced. Hence, it is preferable that the surface of the shoulder attachment portion 11a which comes into contact with the shoulder is at least soft and flexible. In FIG. 6(c), the surface of the shoulder attachment portion 11a is formed by a skin member 11d shaped like a bag, and the skin member 11d is filled with an elastic material 11e made of polyurethane or the like. Further, into the elastic material 11e, a core material having a suitable hardness may be inserted through a center part of the elastic material 11e, though the core material is not shown in the figure.

FIG. 6(d) is a front view of still another variation 1C of the first layer. In FIG. 6(d), a front-side linking portion 15 is provided which extends across the breast in the rightward and leftward directions and links front-end parts of the right and left shoulder attachment portions 11a and 11b. The front-side linking portion 15 enables the patient to be sufficiently stably fitted with the first layer by using only the armpit band portion 12b on the unaffected-part side without an armpit band portion on the affected-part side. Since no armpit band portion is provided on the affected-part side, the patient can take a simple-pendulum exercise smoothly without interference by an armpit band portion. Besides, the front-side linking portion 15 may also be provided with an adjustment fitting 16 for adjusting the length thereof.

Furthermore, a third layer as an additional component element used during a pause in the treatment, as well as the first layer and the second layer, may be provided, though the third layer is not shown in any figure. The third layer may have any shape, as long as it has the function of suppressing the simple-pendulum motion which is made using the second layer by the patient and immobilizing the upper extremity of the patient fitted with the second layer.

In an example, the third layer is a lateral belt which has a great width. With the upper arm on the affected-part side hanging down along the side of the trunk, the wide lateral belt is horizontally wound around the trunk and the upper arm on the affected-part side. In another example, in addition to the wide lateral belt, a second belt may be employed which is a transverse belt supporting the forearm on the affected-part side. In an example, the second belt is fitted to the patient in the following way. An end of the transverse belt is fixed to the front end of the shoulder attachment portion 11b on the unaffected-part side of the first layer. Then, the transverse belt crosses the front of the trunk obliquely from the front end of the shoulder attachment portion 11b toward the radial side of the forearm on the affected-part side, and runs from the radial side of the forearm across the lower surface of the forearm toward the ulnar side of the forearm adjacent to the elbow. The other end of the transverse belt is fixed to a part of the lateral belt on the back side.

The present disclosure may include one or more of the following concepts:

A. A shoulder brace for a simple-pendulum motion which is fitted to a patient having an externally injured shoulder in a physiological reference position where the elbow joint of the patient is flexed by an angle of 90° in the frontward direction and the shoulder is internally rotated by an angle of 30°, comprising:

a first layer (1) including at least: shoulder attachment portions (11a, 11b) attached to both shoulders respectively, the shoulder attachment portions (11a, 11b) each having a predetermined width and being arranged in the frontward and backward directions; and a back-side linking portion (13) extending in the rightward and leftward directions and linking back-end parts of the right and left shoulder attachment portions (11a, 11b); and a second layer (2) including at least a ringed sling (21) having a predetermined width, the sling (21): running below from the front end of a shoulder portion (21a) of the sling (21), the shoulder portion (21a) being placed on the shoulder attachment portion (11a) of the first layer (1) on the affected-part side, up to the ulnar side of the forearm adjacent to the elbow; running from the ulnar side of the forearm across the lower-surface side of the forearm up to the radial side of the forearm; running from the radial side of the forearm across the front of the upper arm; and running through the armpit up to the back end of the shoulder portion (21a),
wherein the patient fitted with the shoulder brace is able to take a simple-pendulum exercise in the frontward and backward directions while retaining the forearm at the shoulder internal-rotation angle of the physiological reference position.

B. The shoulder brace for a simple-pendulum motion according to paragraph A, wherein the second layer (2) is provided with a forearm trough (22) for supporting the forearm, and the sling (21) runs across the lower-surface side of the forearm trough (22).

C. The shoulder brace for a simple-pendulum motion according to paragraphs A or B, wherein the first layer (1) is provided with armpit band portions (12a, 12b) each linking, through the armpit, the front end and the back end of each of the right and left shoulder attachment portions (11a, 11b) respectively.

D. The shoulder brace for a simple-pendulum motion according to paragraphs A or B, wherein the first layer (1) is provided with:
an armpit band portion (12b) linking, through the armpit, the front end and the back end of the shoulder attachment portion (11b) of the first layer (1) on the unaffected-part side alone; and
a front-side linking portion (15) extending in the rightward and leftward directions and linking front-end parts of the right and left shoulder attachment portions (11a, 11b).

The shoulder brace for a simple-pendulum motion according to the present invention has been described so far with reference to the above embodiment and variations. However, various changes and modifications will be made unless such changes and modifications depart from the scope of the present invention. Besides, although the materials of the individual component elements are not particularly limited, suitable materials should be chosen for the purpose of fulfilling the functions of the present invention.

PRACTICAL EXAMPLE

<Patient and Case>
Female, 75 years old
Proximal humerus fractures on the right and left (11-B1.1 under the AO classification)
<Patient Fitted with Shoulder Brace>
The patient was fitted with the shoulder brace on the day following an operation. Both affected shoulders were each fitted with the second layer. The patient was allowed to use the hands. The patient fitted with the shoulder brace took simple-pendulum exercises in a sitting or standing position.
<Result>
Eight weeks after the operation, the patient was able to move the shoulders over almost the full range of motion thereof without feeling a pain. The rehabilitation exercises after the operation produced the desired result.

The invention claimed is:

1. A shoulder brace for a simple-pendulum motion adapted to be fitted to a patient having an externally injured shoulder in a physiological reference position where an elbow joint of the patient is flexed by an angle of 90° and the externally injured shoulder is internally rotated by a shoulder internal-rotation angle of 30°, the shoulder brace comprising:
a first layer including a first shoulder attachment portion and a second shoulder attachment portion each configured to be attached to a respective shoulder of the patient, the first and second shoulder attachment portions each having a predetermined width and a length having an anterior end and a posterior end, the length arranged in an anterior-posterior direction, and a posterior-side linking portion extending in a mediolateral direction and linking the posterior ends of the first and second shoulder attachment portions; and
a second layer including a ringed sling having a predetermined width, the ringed sling including a shoulder portion disposed on the first shoulder attachment portion of the first layer, wherein the ringed sling is configured to run downward from an anterior end of the shoulder portion of the ringed sling to an ulnar side of a forearm adjacent to an elbow of the patient, configured to run from the ulnar side of the forearm across a lower-surface side of the forearm up to a radial side of the forearm, configured to run from the radial side of the forearm across an anterior side of an upper arm of the patient, and configured to run through an armpit of the patient up to a posterior end of the shoulder portion;
wherein the shoulder brace is configured to enable the patient to perform a simple-pendulum exercise in the anterior-posterior direction while retaining the forearm at the shoulder internal-rotation angle of the physiological reference position.

2. The shoulder brace for a simple-pendulum motion according to claim 1, wherein the first layer is provided with first and second armpit band portions, each configured to link the anterior end and the posterior end of the first and second shoulder attachment portions, respectively.

3. The shoulder brace for a simple-pendulum motion according to claim 1, wherein the first layer is provided with:
an armpit band portion linking, the anterior end and the posterior end of the second shoulder attachment portion of the first layer; and
an anterior-side linking portion extending in a mediolateral direction and linking respective anterior ends of the first and second shoulder attachment portions.

4. The shoulder brace for a simple-pendulum motion according to claim 1, wherein the second layer includes a forearm trough configured to support the forearm, and the ringed sling runs across a lower-surface side of the forearm trough.

5. The shoulder brace for a simple-pendulum motion according to claim 4, wherein the first layer is provided with first and second armpit band portions, each linking the anterior end and the posterior end of the first and second shoulder attachment portions, respectively.

6. The shoulder brace for a simple-pendulum motion according to claim 4, wherein the first layer is provided with:
an armpit band portion linking the anterior end and the posterior end of the second shoulder attachment portion of the first layer; and
a anterior-side linking portion extending in a mediolateral direction and linking respective anterior ends of the first and second shoulder attachment portions.

* * * * *